(12) United States Patent
Kim et al.

(10) Patent No.: US 7,635,591 B2
(45) Date of Patent: Dec. 22, 2009

(54) METHOD FOR DIFFERENTIATING MESENCHYMAL STEM CELL INTO NEURAL CELL AND PHARMACEUTICAL COMPOSITION CONTAINING THE NEURAL CELL FOR NEURODEGENERATIVE DISEASE

(75) Inventors: Hyun-Soo Kim, 313-1003, Daewoo Dongsin Apt., 956-2, Youngtong-dong, Youngtong-gu, Suwon-si, Kyunggi-do, 443-810 (KR); Young-Mo Kang, Suwon-si (KR); Kyung-Bock Lee, Suwon-si (KR); Sang-Kyo Park, Suwon-si (KR); Sang-Kap Lee, Daegu-si (KR)

(73) Assignees: FCB Pharmicell Co., Ltd., Sungnam-si (KR); Hyun-Soo Kim, Suwon-si (KR)

( * ) Notice: Subject to any disclaimer, the term of this patent is extended or adjusted under 35 U.S.C. 154(b) by 150 days.

(21) Appl. No.: 10/595,620

(22) PCT Filed: Oct. 29, 2003

(86) PCT No.: PCT/KR03/02302

§ 371 (c)(1),
(2), (4) Date: May 1, 2006

(87) PCT Pub. No.: WO2005/040362

PCT Pub. Date: May 6, 2005

(65) Prior Publication Data

US 2007/0054399 A1   Mar. 8, 2007

(51) Int. Cl.
*C12N 5/00* (2006.01)
*C12N 5/02* (2006.01)
*C12N 5/08* (2006.01)

(52) U.S. Cl. .................. 435/377; 435/325; 435/372

(58) Field of Classification Search .................. None
See application file for complete search history.

(56) References Cited

U.S. PATENT DOCUMENTS

| | | | |
|---|---|---|---|
| 5,942,225 A | 8/1999 | Bruder et al. | |
| 6,214,334 B1 | 4/2001 | Lee et al. | |
| 7,015,037 B1 * | 3/2006 | Furcht et al. | 435/372 |
| 2006/0134078 A1 * | 6/2006 | Kokuzawa et al. | 424/93.21 |

FOREIGN PATENT DOCUMENTS

| | | |
|---|---|---|
| KR | 10-2002-0082239 A | 10/2002 |
| WO | 96/15226 A1 | 5/1996 |
| WO | 02/086108 A1 | 10/2002 |

OTHER PUBLICATIONS

D. Woodbury et al., "Adult Rat and Human Bone Marrow Stromal Cells Differentiate Into Neurons", Journal of Neuroscience Research 61: 364-370, 2000.

Schuldiner et al.; "Effects of eight growth factors on the differentiation of cells derived from human embryonic stem cells"; PNAS; Oct. 10, 2000; vol. 97, No. 21; pp. 11307-11312.

K. Sugaya; "Neuroreplacement therapy and stem cell biology under disease conditions"; Cell. Mol. Life Sci.; 2003; vol. 60; pp. 1891-1902.

Sanchez-Ramos et al.; "Adult Bone Marrow Stromal Cells Differentiate into Neural Cells in Vitro"; Experimental Neurology; 2000; vol. 164; pp. 247-250.

* cited by examiner

*Primary Examiner*—Fereydoun G Sajjadi
(74) *Attorney, Agent, or Firm*—Sughrue Mion, PLLC

(57) ABSTRACT

The present invention provides a method of differentiating and proliferating a mesenchymal stem cell into the neural cell by culturing in a medium comprising an epidermal growth factor and a hepatocyte growth factor after confluent culture of the mesenchymal stem cell. The present invention provides more effective method of differentiating and proliferating the mesenchymal stem cell or the mononuclear cell comprising the mesenchymal stem cell into the neural cell with a neuron and an astrocyte in terms of time, efficiency and maturity as compared with conventional methods.

5 Claims, 20 Drawing Sheets

[FIG. 1]
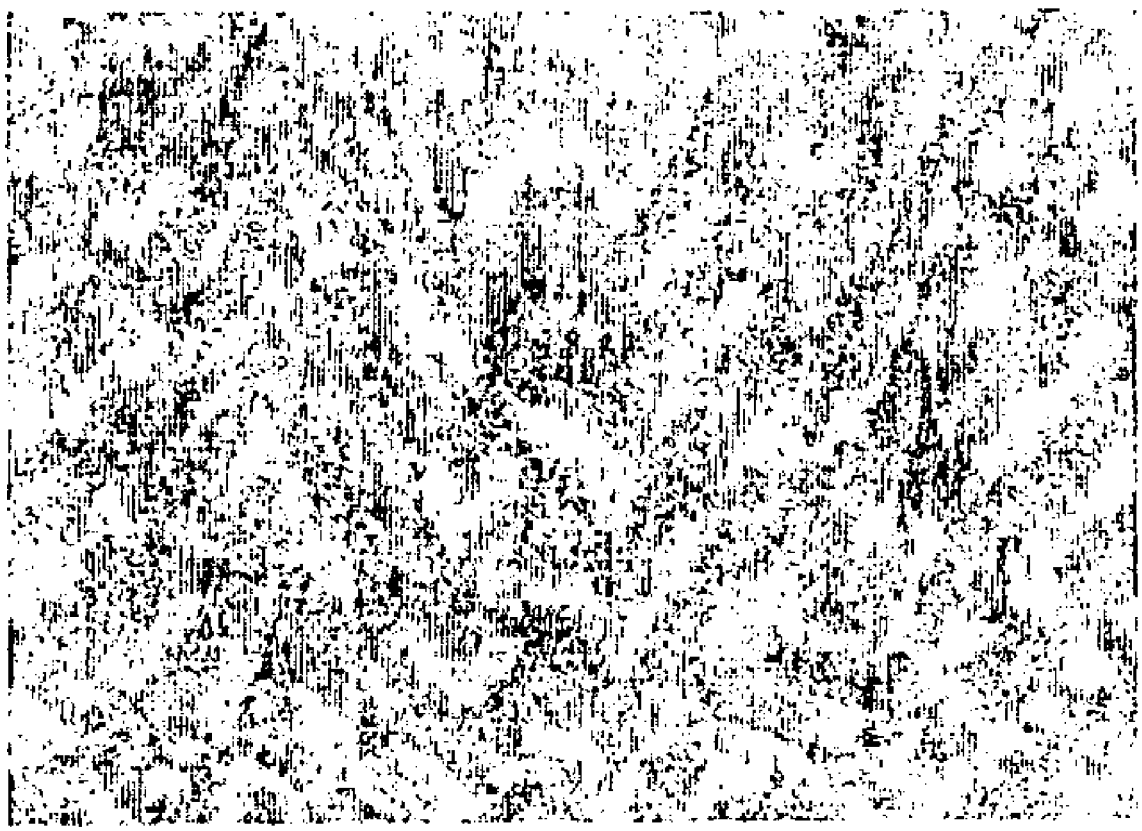

[FIG. 2]
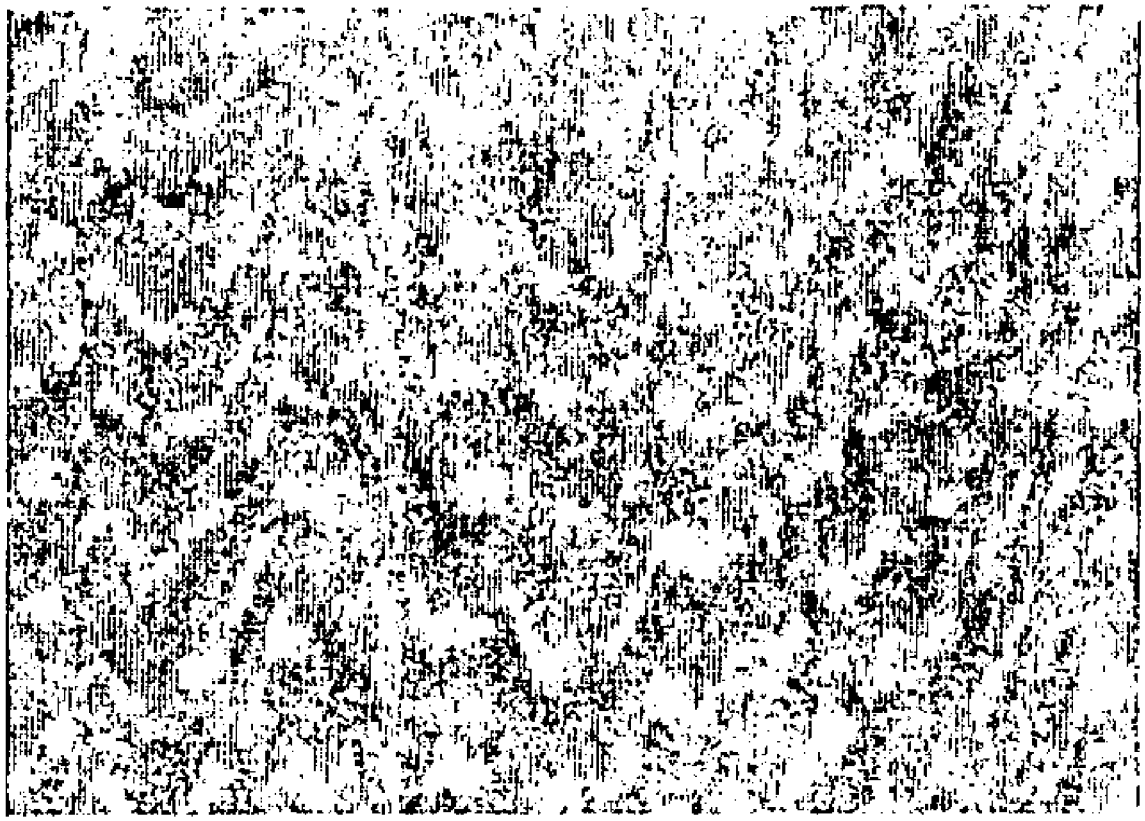

[FIG. 3a]
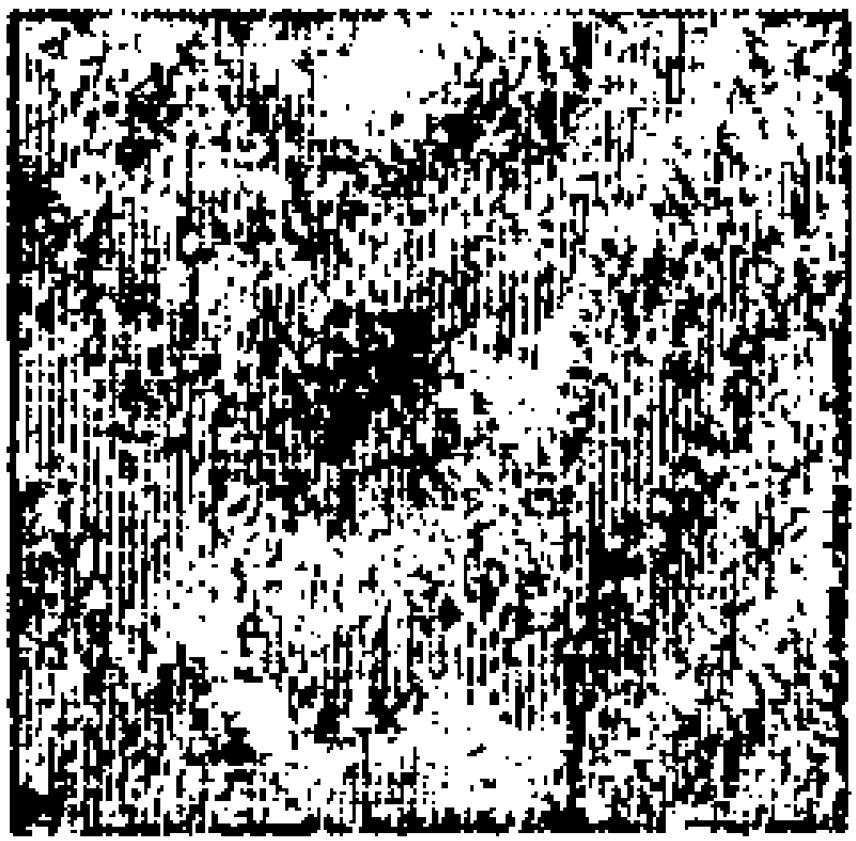

[FIG. 3b]

[FIG. 4a]
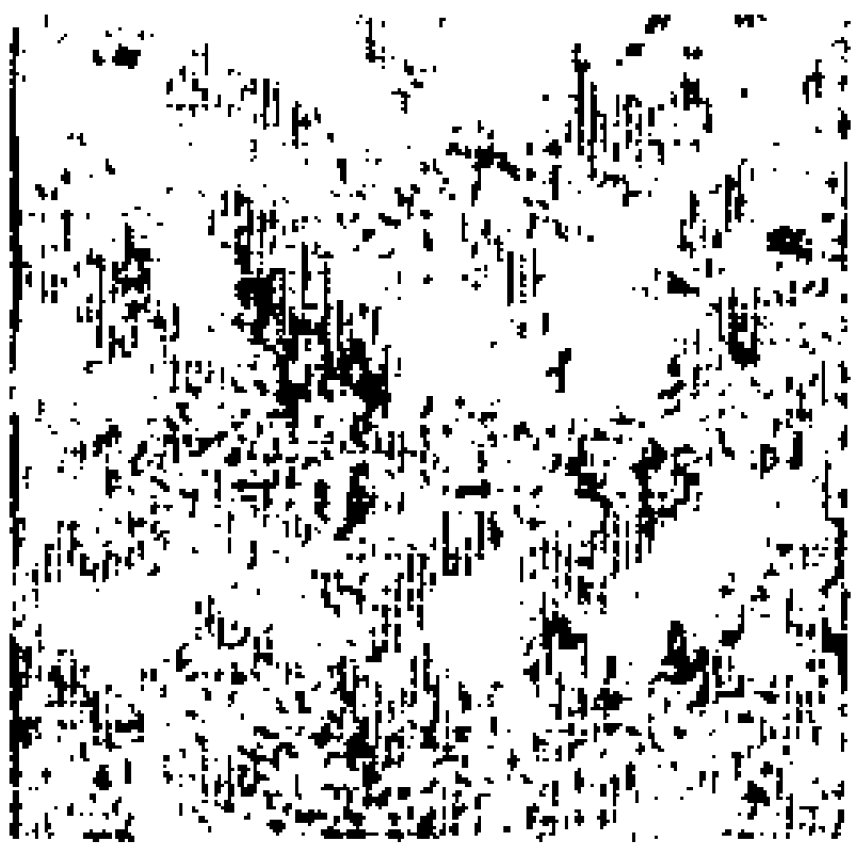

[FIG. 4b]
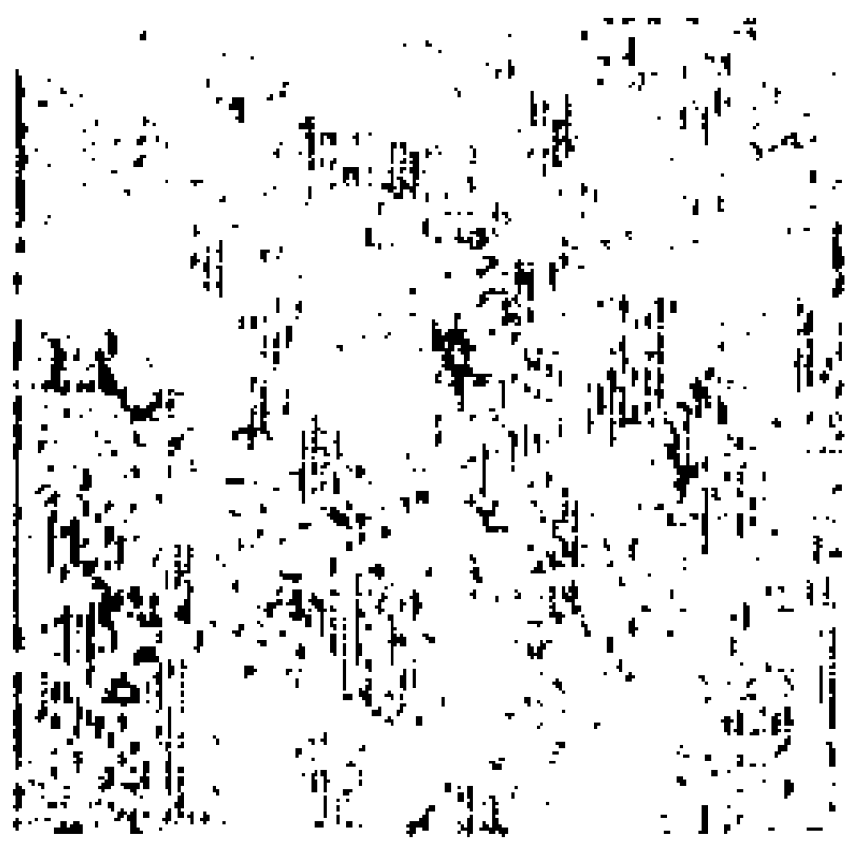

[FIG. 4c]

[FIG. 4d]
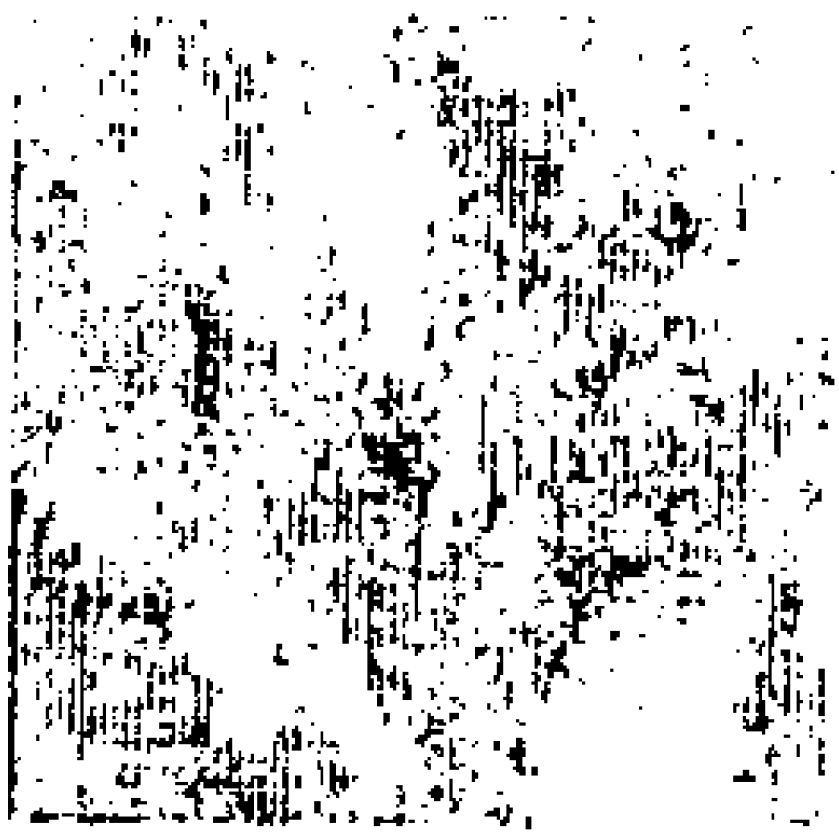

[FIG. 5a]
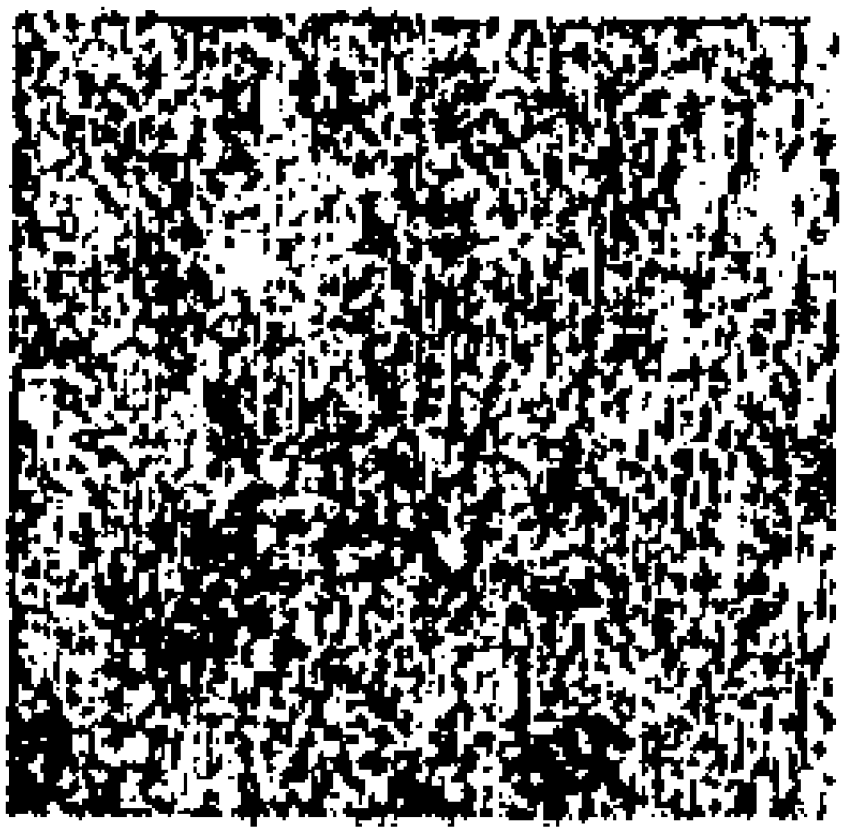

[FIG. 5b]
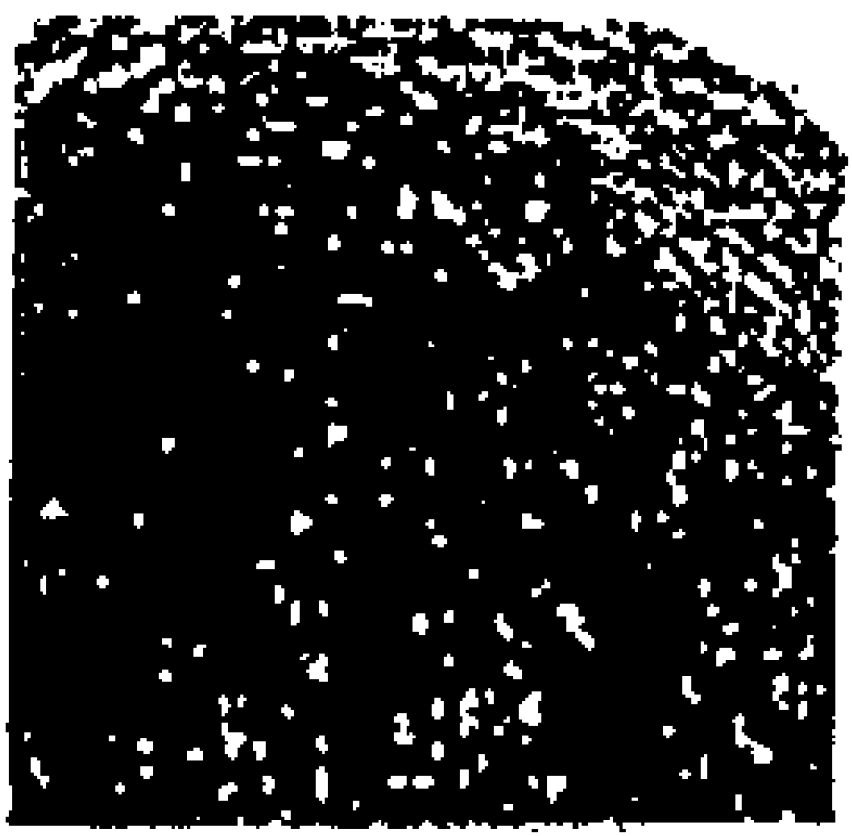

[FIG. 5c]
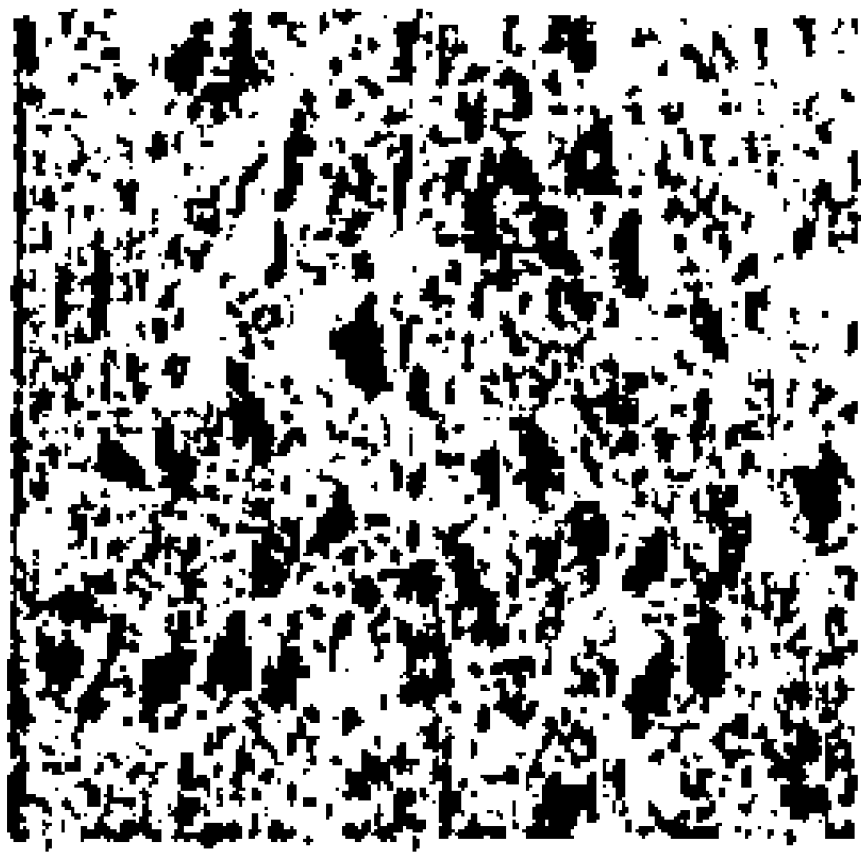

[FIG. 6]

[FIG. 7]

[FIG. 8a]
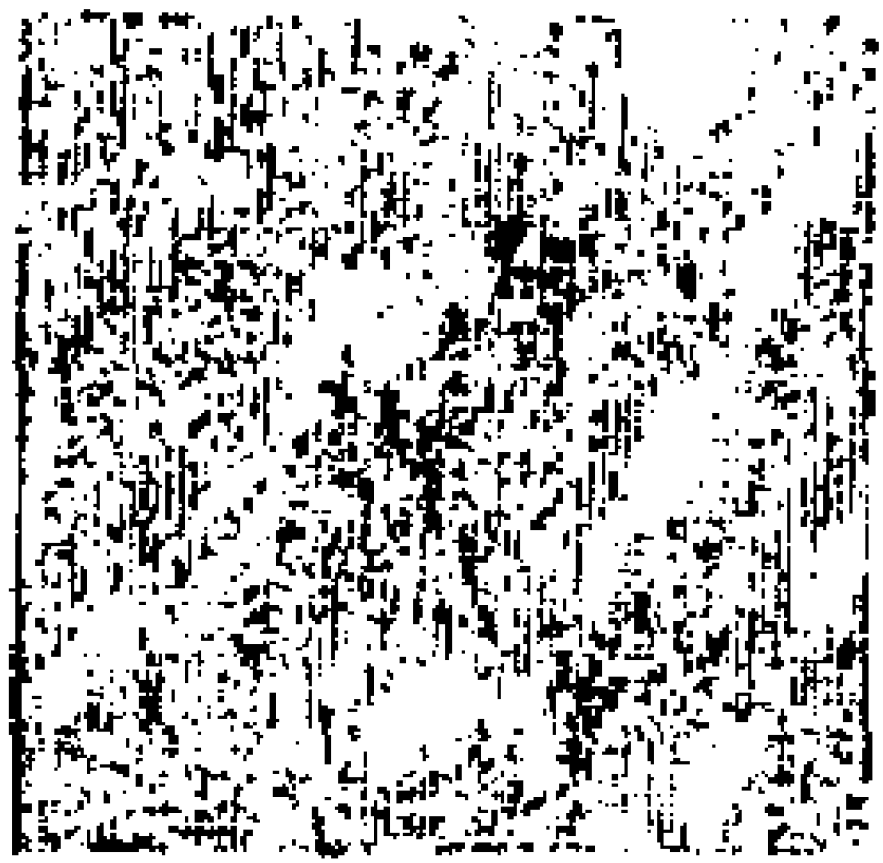

[FIG. 8b]

[FIG. 8c]
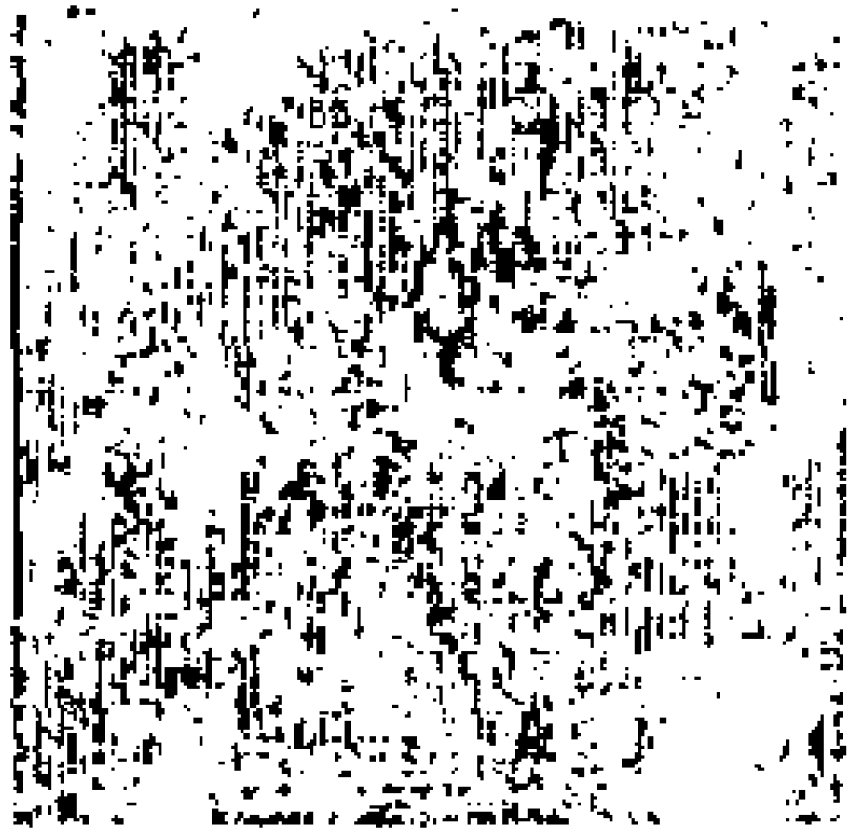

[FIG. 8d]
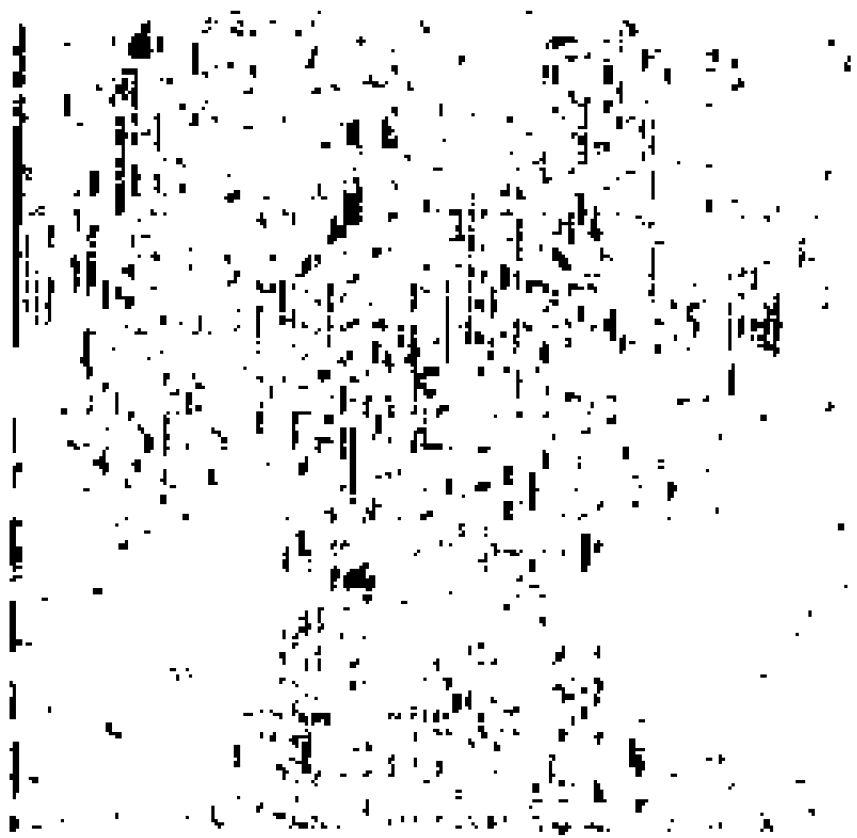

[FIG. 9a]

[FIG. 9b]

[FIG. 9c]
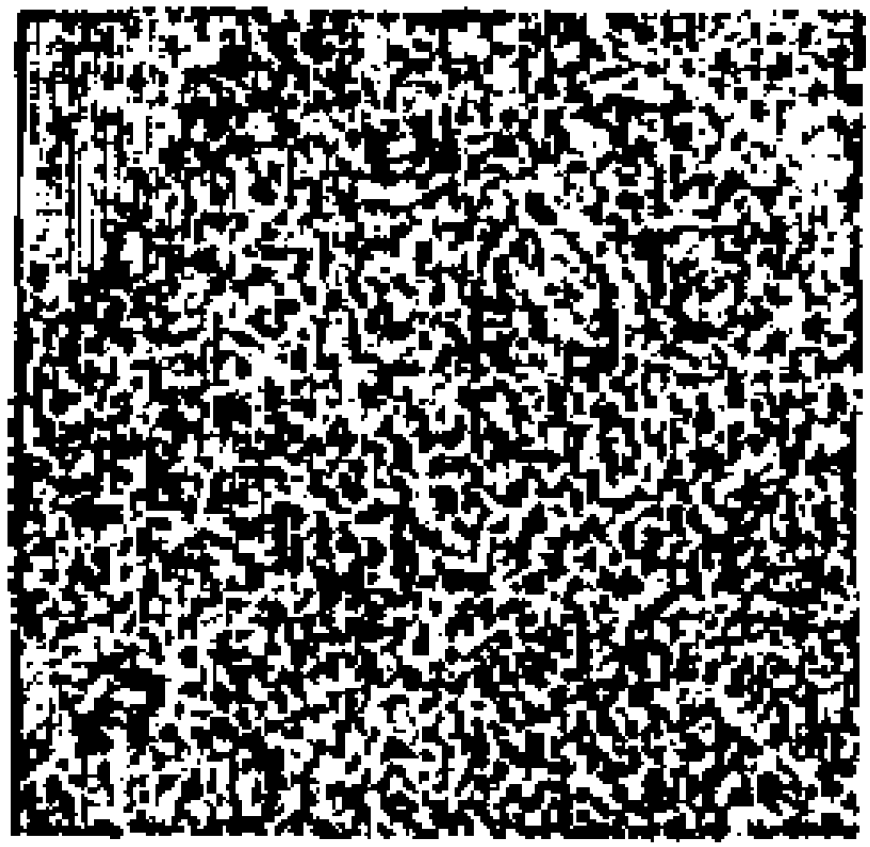

METHOD FOR DIFFERENTIATING MESENCHYMAL STEM CELL INTO NEURAL CELL AND PHARMACEUTICAL COMPOSITION CONTAINING THE NEURAL CELL FOR NEURODEGENERATIVE DISEASE

TECHNICAL FIELD

The present invention relates to a method of differentiating of a mesenchymal stem cell into a neural cell, and a pharmaceutical composition comprising the neural cell prepared by the method for neurodegenerative disease. More particularly, the present invention relates to a method of differentiating of a mesenchymal stem cell into a neural cell prepared by culturing in a medium comprising a epithermal growth factor and a hepatocyte growth factor after confluent culturing the mesenchymal stem cell for one day, and a pharmaceutical composition comprising the neural cell prepared by the method or alternative methods, for neurodegenerative disease.

BACKGROUND ART

Since a mesenchymal stem cell recently has been isolated successfully from human, a clinical application of the mesenchymal stem cell has been brought to a focus. Particularly, the clinical application of the mesenchymal stem cell is used as cell donor for a cell replacement therapy. The cell replacement therapy is presented for effectively treating cell deficiency caused by neurodegenerative diseases such as Parkinson's disease and Alzheimer's disease known by incurable disease, ischemic and hemorrhagic stroke, traumatic disease and spinal cord injury, which are caused by destruction and permanent functional disorder of cells consisting of tissues.

However, cell replacement therapy has a limitation in practical application. That is, a conventional method of implanting cells differentiated fully into donor's tissues to patients is difficult to obtain sufficient amount of the cells to give the patients.

In order to solve the above-mentioned problems, differentiating the mesenchymal stem cell into a tissue-specific cell or inducing differentiation after isolating and proliferating the tissue-specific stem cell may be used as the cell replacement therapy.

Implanting a neural cell differentiated from a mesenchymal stem cell in one human into another human, however, is practically difficult, and creates immunological reactions in case of implanting the neural cell between male and female cell donors.

Until now, differentiations of a mesenchymal stem cell of a rat into a hematopoietic cell, a myocardial cell, an islet of Langerhans and a neural cell are proved in culture flask. Studies such as a study on implanting an oligodendrocyte into a rat and being increased to create myelin after inducing to differentiate into the oligodendrocyte as a cell creating myelin from the mesenchymal stem cell (Brustle et al., Science 285: 754-756), a study on implanting an insulin secreting cell, differented from the mesenchymal stem cell, into a diabetic rat and regulating blood sugar lever (Soria et al., Diabetes 49:11157-162, 2000), a study on implanting a neural cell that is differentiated from the mesenchymal stem cell, into a spinal cord injured rat and confirming to improve motor disturbance spinal cord injured (McDonald et al., Nat. Med. 5(12):1410-1412, 1999), etc., represent a method of implanting of the cells that are differentiated from the mesenchymal stem cell, for effectively treating diseases due to deficiency of cell.

However, isolation of the mesenchymal stem cell has been accomplished just recently and differentiation of the mesenchymal stem cell into the other cells except the neural cell in culture flask has been yet reported, such that the clinical application of the tissue-specific cell differentiated from the mesenchymal stem cell for the cell replacement therapy is possible, but is not practical.

Although a method of differentiating a cell from the mesenchymal stem cell as for the cell replacement therapy is thought as the most effective method until now, a risk of other cells mixed due to low efficiency of differentiating into the tissue-specific cell from the mesenchymal stem cell except immunological reactions in case of implanting into a patient still exists, such that studies on delicate differentiation are required for safe clinical application.

A method of using the tissue-specific stem cell for the cell replacement therapy also has a problem such as differentiating into undesired cells due to modifying of differentiation potential when the tissue-specific stem cell is cultured for a long time, decreasing of proliferation rate of a cell. Moreover, a neural cell for treating neurodegenerative disease such as Parkinson's disease is required to be implanted. Considering that the neural cell is obtained mainly by differentiating and proliferating a neural stem cell from fetal brain since the neural cell is difficult to be obtained directly from patients, implanting a neural cell is a disadvantage. About two fetal brains are required to treat one patient in such a case of above. Implanting the neural cell has problems such as insufficient supply of the neural cell and unethical act, differentiation of the neural stem cell into an astrocyte than the neural cell, and generation of immunological reaction.

Accordingly, if a method of treatment using the neural cell differentiated from the mesenchymal stem cell is possible, problems such as difficulty in obtaining sufficient cells and generating immunological reaction may be solved. Whether the mesenchymal stem cell as a mesoderm may be differentiated into the neural cell is still in question, but trans-differentiation was recently reported and the possibility of differentiation of the mesenchymal stem cell is increased.

Formerly, a hepatocyte is known to be differentiated into only specific class of a tissue cell. It was reported that the mesenchymal stem cell formed in vitro colonies in a medium comprising growth factors such as basic fibroblast growth factor, transforming growth factor, epithermal growth factor etc. (Kuznetsov et al., Br. J. Haematol. 97:561, 1997; Van den Bos C et al., Human Cell 10:45, 1997). In addition, about a third of the firstly anchored cells with multi-differentiative potential were differentiated into desmoplastic cells such as osteoblast, chondroblast, adipocyte etc. (Pttenger M F et al., Science 279:1528, 1998), and a bone marrow was resource of a myogenic precursor cell for forming new muscles (Ferrari G et al., Science 279:1528, 1998).

However, according to recent consecutive studies, it was reported that the mesenchymal stem cell might be differentiated into not only desmoplastic cells, but also into neural cells. For example, it was reported that the mesenchymal stem cell was differentiated into the neural cell and the astrocyte by culturing in medium comprising retinoic acid and BDNF (brain-derived neurotrophic factor) (Sanchez-Ramos et al., Exp. Neurology 164:247-256, 2000) and into the neural cell by culturing in medium comprising antioxidative substance such as mercaptoethanol and DMSO (dimethyl sulfoxide) (Dale Woodbury et al., J. Neuro. Res. 61:364-370, 2000).

When a chemical reagent such as DMSO is used to induce differentiation, however, toxicity of DMSO may alter the mesenchymal stem cell such that a safer method is required.

The inventor of the present invention studied a safe and effective method of differentiating of the mesenchymal stem cell into the neural cell, and applied for a patent that was "method of differentiating the mesenchymal stem cell into the neural cell" at Korean patent number 2001-21064. The patent is related to a method of differentiating and proliferating the mesenchymal stem cell into the neural cell by culturing in medium comprising an epithermal growth factor and a hepatocyte growth factor.

The method of differentiating and proliferating of the mesenchymal stem cell into the neural cell has problems not only with low rate but also about 80% efficiency of differentiation. Further, culturing for four weeks is required due to low differentiation rate when a cell during differentiating and proliferating is cultured such that morphological alteration occurs. Thus, problems such as contamination and a large consumption of reagents, equipments and time, are generated.

The method in Korean patent number 2001-21064 is proposing the possibility that the neural cell that is differentiated from the mesenchymal stem cell is useful for treating neurodegenerative disease such as Parkinson's disease, Alzheimer, Pick's disease, Huntington's disease, amyotrophic lateral sclerosis, and ischemic and hemorrhagic brain disease, however, in vitro test, animal test or clinical test has yet performed and thus pharmacological effect of the neural cell also has yet confirmed.

To solve the problems, the inventor completed the present invention by studying on a method of improving differentiation rate and efficiency, and a test of pharmacological effect.

DISCLOSURE OF THE INVENTION

Technical Problem

Accordingly, it is an object of the present invention to provide a method of differentiating and proliferating a mesenchymal stem cell into a neural cell by culturing in a medium comprising an epithermal growth factor and a hepatocyte growth factor, the mesenchymal stem cell being cultured in the medium after confluent culturing the mesenchymal stem cell.

It is another object to provide a pharmaceutical composition comprising a neural cell for treating neurodegenerative disease such as Parkinson's disease, Alzheimer's disease, Pick's disease, Huntington's disease, amyotrophic lateral sclerosis, ischemic and hemorrhagic brain disease, and traumatic central nervous system disease such as spinal cord injury.

Technical Solution

Hereinafter, the present invention is described in details.

The present invention provides a method of differentiating a mesenchymal stem cell into a neural cell by confluent culturing in a medium comprising an epithermal growth factor and a hepatocyte growth factor.

The mesenchymal stem cell is usually cultured in state of maintaining that the rate of cells that take the surface of the medium is about 70% by count for continuous growth. However the mesenchymal stem cell of the present invention is confluent cultured continuously after taking of the cell completely the surface of the medium, which is object to induce differentiation than proliferation. Therefore, the differentiation may be carried out rapidly and effectively when stimulation of differentiation is applied after confluent culturing as according to the present invention.

Preferably, the mesenchymal stem cell is confluent cultured for about 1 to about 50 hours, and then is cultured respectively in the medium comprising the epithermal growth factor of about 1 to about 10,000 ng/ml and the hepatocyte growth factor of about 1 to about 10,000 ng/ml for 1 week or more.

More preferably, the mesenchymal stem cell is confluent cultured for about 24 hours, and then is cultured respectively in the medium comprising the epithermal growth factor of about 10 ng/ml and the hepatocyte growth factor of about 10 ng/ml for 1 week or more.

When the mesenchymal stem cell is cultured as in the above-mentioned condition, a few mesenchymal stem cells form a neural cell colony after about 4 days and the neural cell colony proliferate continuously such that a large quantity of the neural cell may be formed after about 1 week.

In particular, the neural cell that is fully differentiated and proliferated in the medium comprising the epithermal growth factor and the hepatocyte growth factor for about 2 weeks is proliferated continuously without altering a character of the neural cell in a medium comprising only the epithermal growth factor However, a neural cell differentiated fully for about 2 weeks, differentiates by culturing in a medium comprising only the hepatocyte growth factor such that the neural cell count is decreased due to progressing of only differentiating of the neural cell. Therefore, culturing the neural cell that is differentiated fully, in the medium comprising only the epithermal growth factor is preferable after about 2 weeks.

The mesenchymal stem cell in the present invention may be obtained by isolating from a human bone marrow. A hematopoietic stem cell is differentiated into a blood cell when a mononuclear cell is isolated from the bone marrow, such that the mesenchymal stem cell is obtained by a method of isolating only the stem cell as an unlimited proliferation cell that is remained.

However, culturing total mononuclear cells isolated from the bone marrow as the above-mentioned method without isolation of the mesenchymal stem cell from mononuclear cells shows same conclusion—producing a large quantity of the neural cells—such that using only the mesenchymal stem cell is not required.

As mentioned above, when the mesenchymal stem cell is cultured in the medium comprising the epithermal growth factor and the hepatocyte growth factor, about 90% by count of the mesenchymal stem cell is differentiated into the neural cell, about 70% by count of the neural cell is neuron, about 30% by count is the astrocyte, and none is a microglial cell.

In the present invention, the neural cell includes neuron, astrocyte and microglial cell.

The neural cell that is differentiated from the mesenchymal stem cell by the above-mentioned method in the present invention, may be used as a pharmaceutical composition for treating neurodegenerative disease in the cell replacement therapy. Accordingly, the present invention provides the pharmaceutical composition comprising the neural cell prepared by the method of the present invention for treating neurodegenerative disease such as Parkinson's disease, Alzheimer, Pick's disease, Huntington's disease, Amyotrophic lateral sclerosis, Ischemic and hemorrhagic brain disease, traumatic central nervous system disease, and motor disturbance by injuring the vertebra.

The pharmaceutical composition comprising the neural cell for treating neurodegenerative disease may be administered by formulating a unit dosage suitable for administrating to human by conventional methods in pharmaceutical field. Injection as non-oral administration is preferred.

In addition to the neural cell of the pharmaceutical composition, the above formulation may contain one or more inactivated carriers that are permitted pharmaceutically. Examples of the inactivated carriers include preservative, analgesic controller, solublizer, stabilizer, etc., as an injection application, and gasifier, bulking agent, lubricant, stabilizer, etc., as a topical application.

The pharmaceutical formulation may be used for non-oral administration, for example intravenous, subcutaneous, intraperitoneal administration or topical application.

For example, a clinical method known by Douglas Kondziolka (Pittsburgh, 1998) may be used. The method includes cutting patient's skull about 1 cm diameter of pea size and injecting the neural cell solution mixed with Hank's balanced salt solution (HBSS) into 3 places. In a method of injecting the neural cell solution, a syringe with long needle and stereotactic frame are used for an injection. The neural cell may be injected directly or through vein and artery Preferably, a dosage of the neural cell is about $1 \times 10^6$ to about $1 \times 10^9$ cells, and may vary in accordance with a kind of disease, a degree of seriousness of disease, dosage route, weight, age and sex of patient.

As mentioned above, it was known that the mesenchymal stem cell has been differentiated into the neural cell by culturing in the medium comprising the epithermal growth factor and the hepatocyte growth factor in the prior inventions. However, it is first known that culturing in the medium comprising the epithermal growth factor and the hepatocyte growth factor after confluent culture as pre-treatment may improve differentiation speed within one week, differentiation rate and maturity of the neural cell according to the present invention.

The present invention compared each amount of the mononuclear cell isolated from the bone marrow to be proliferated and differentiated into the neural cell in case of culturing in the medium comprising the epithermal growth factor and the hepatocyte growth factor after confluent culture for about 24 hours, and in case of culturing in a medium comprising one of the epithermal growth factor and the hepatocyte growth factor without confluent culture, respectively. As a result, in case of culturing in the medium comprising the epithermal growth factor and the hepatocyte growth factor after confluent culture for about 24 hours, the neural cell colony began to be formed after about 1 week and continued to proliferate even after about 2 weeks. The mononuclear cell was not differentiated into the neural cell in case of culture in the medium comprising only the epithermal growth factor, and was differentiated early and proliferated in case of culturing in the medium comprising only the hepatocyte growth factor.

Accordingly, when the mesenchymal stem cell or the mononuclear cell derived from the bone marrow is differentiated and proliferated into the neural cell, the epithermal growth factor inducing proliferation, the hepatocyte growth factor inducing differentiation, and confluent culture for about 24 hours stimulate fast effect of the growth factors. Sufficient amount of the neural cell may not be obtained from only one of the growth factors.

In the present invention, the mesenchymal stem cell or the mononuclear cell derived from the bone marrow is cultured in the medium comprising the epithermal growth factor and the hepatocyte growth factor for about 2 weeks after confluent culture for about 24 hours, and then the differentiated and proliferated cell is separated as a single cell and observed with an optical microscope. As a result, a neuron with long axon and short dendrite, and an astrocyte with only short dendrite may be observed.

By performing immunocytochemistry stain of the differentiated and proliferated cells according to the present invention, a neuron marker such as NeuN, NSE and MAP-2, and an astrocyte marker such as GFAP are stained positively, which may confirm that the differentiated and proliferated cells are consist of the neuron and the astrocyte. The microglial cell marker such as OX-42 is stained negatively, which may confirm that the cell is not differentiated into the microglial cell.

When the mesenchymal stem cell or the mononuclear cell derived from the bone marrow is confluent-cultured in the medium comprising the epithermal growth factor and the hepatocyte growth factor for about 24 hours, after about 2 weeks, about 90% by count of cell is differentiated into the neural cell, about 70% by count of the neural cell is neuron, about 30% by count is the astrocyte. After the mesenchymal stem cell or the mononuclear cell is fully differentiated and proliferated after about 2 weeks, the mesenchymal stem cell or the mononuclear cell maintains a shape of the neural cell and proliferates continuously in the medium comprising only the epithermal growth factor. In the medium comprising only the hepatocyte growth factor, the mesenchymal stem cell or the mononuclear cell is merely differentiated, so that the mesenchymal stem cell or the mononuclear cell is not continuously proliferate.

The mesenchymal stem cell is only isolated from the mononuclear cells so that it is confirmed whether the neural cell, derived from the mononuclear cell in the bone marrow by culturing in the medium comprising the epithermal growth factor and the hepatocyte growth factor, is differentiated from the mesenchymal stem cell. The stem cell is classified into the hematopoietic stem cell and the mesenchymal stem cell derived from the mononuclear cells in the bone marrow. The hematopoietic stem cell is easily differentiated into blood cells under general culture condition, such that the stem cell that is continuously proliferated after about 1 to about 2 weeks may be the mesenchymal stem cell. After isolating only the mesenchymal stem cell that may be subcultured more than 20 times, the experiment of differentiating into various connective tissues is carried out so that the experiment may confirm that the mesenchymal stem cell has an ability of differentiating into various connective tissue cells. A result of the experiment has confirmed that the mesenchymal stem cell may differentiate into various connective tissue cells.

Further, it is confirmed that the mesenchymal stem cell is differentiated into the neural cell and the astrocyte, and is proliferated in the medium comprising the epithermal growth factor and the hepatocyte growth factor by the experiment of differentiating and proliferating into the neural cell, optical microscope and immunocytochemistry like as the bone marrow-derived mononuclear cell

BRIEF DESCRIPTION OF THE DRAWING

FIG. 1 shows a photograph of an anchored cell when a bone marrow-derived mononuclear cell is cultured in a medium comprising about 10 ng/ml of an epithermal growth factor and about 20 ng/ml of a hepatocyte growth factor, respectively, for about 1 week after confluent culture for about 24 hours through optical microscope (×100).

FIG. 2 shows a photograph of a neural cell when the bone marrow-derived mononuclear cell is cultured in the medium comprising about 10 ng/ml of an epithermal growth factor and about 20 ng/ml of a hepatocyte growth factor, respectively, for about 2 weeks after confluent culture for about 24 hours through optical microscope (×100).

FIG. 3 shows a photograph of the differentiated and isolated neural cell from the bone marrow-derived mononuclear cell in FIG. 2 through optical microscope; FIG. 3a shows a neuron and FIG. 3b shows an astrocyte.

FIG. 4 shows a photograph of the differentiated neural cell from the bone marrow-derived mononuclear cell in FIG. 2 by immunocytochemistry; FIG. 4a shows positively stained cell in NSE, FIG. 4b shows in NeuN, FIG. 4c shows in GFAP, and FIG. 4d shows in MAP-2.

FIG. 5 shows a photograph of the differentiated cell when the bone marrow-derived mononuclear cell is cultured in a medium comprising low concentration of glucose and the mesenchymal stem cell is isolated and differentiated into osteoblasts (FIG. 5a), chondroblasts (FIG. 5b) and fat cell (FIG. 5c) through optical microscope.

FIG. 6 shows a photograph of the mesenchymal stem cell when the mesenchymal stem cell is cultured in the medium comprising about 10 ng/ml of the epithermal growth factor and about 20 ng/ml of the hepatocyte growth factor, respectively, for about 1 week through optical microscope.

FIG. 7 shows a photograph of the proliferated and differentiated neural cell when the mesenchymal stem cell is cultured in the medium comprising about 10 ng/ml of the epithermal growth factor and about 20 ng/ml of the hepatocyte growth factor, respectively, for about 2 weeks through optical microscope.

FIG. 8 shows a photograph of the differentiated neural cell in FIG. 6 by immunocytochemistry; FIG. 8a shows positively stained cell in NSE, FIG. 8b shows in NeuN, FIG. 8c shows in GFAP, and FIG. 8d shows in MAP-2.

FIG. 9 shows a photograph of a rat brain cut after about 2 weeks since a rat induced Ischemic disease is venous-injected at about 3×105 cell of the neural cells from the mesenchymal stem cell through optical microscope; FIG. 9a shows a photograph of a rat brain before inducing local Ischemic disease, FIG. 9b shows a photograph of a rat brain in about 2 weeks after since the neural cells venous-injected after inducing local Ischemic disease, and FIG. 9c shows a enlarged photograph of local Ischemic portion in FIG. 9b.

BEST MODE FOR CARRYING OUT THE INVENTION

Hereinafter, the best mode of the present invention will be described in detail. However, it should be understood that these examples are provided only for illustration of the present invention, but not intended to limit the present invention in any manner.

EXAMPLE 1

Isolation of a Mononuclear Cell in a Bone Marrow

About 10 ml of a bone marrow was obtained from pelvis of healthy applicants and kept in glass tube comprising Heparin. About 30 ml of phosphate buffered saline (PBS) was added to about 10 ml of the bone marrow, about 20 ml of the mixed solution was flowed slowly on about 10 ml of Ficoll-Paque™ plus (1.077 g/ml, Amersham Pharmacia Biotech) solution and centrifuged on density gradient at 2,000 rpm for about 20 minutes. The layer of a mononuclear cell was collected between upper layer and Ficoll-Paque™ plus layer and centrifuged at 1,800 rpm for about 5 minutes. Thus, the mononuclear cell was only obtained.

EXAMPLE 2

Culture of the Mononuclear Cell

The mononuclear cell prepared by Example 1 was inoculated into culture flask of about 1×106 cells/cm$^2$ and after about 4 hours, an unanchored cell was removed by washing with a new basal medium. The new basal medium used Wiliams' E medium (Gibco BRL) comprising 3.5M hydrocortisone (Sigma), fatty acid free bovine serum albumin (Gibco BRL), 50 ng/ml linoleic acid (Sigma), 0.1M CuSO$_4$ 5H$_2$O (Sigma), 50 pM ZnSO$_4$ 7H$_2$O (Sigma), 3 ng/ml H$_2$ SeO$_3$ (Sigma), 1.05 mg/ml NaHCO$_3$ (Sigma), 1.19 mg/ml HEPES (Sigma), 100 U/ml Penicillin (Gibco BRL), 10 mg/ml Streptomycin (Gibco BRL), and 25 g/ml Amphotericin (Gibco BRL).

EXAMPLE 3

Differentiation of the Mononuclear Cell into a Neural Cell without Confluent Culture Example 3 confirmed whether the mononuclear cell cultured in Example 2 was differentiated into the neural cell in a medium comprising about 10 ng/ml of the epithermal growth factor (Gibco BRL) and about 20 ng/ml of the hepatocyte growth factor (R&D systems) without confluent culture. Then the differentiation medium was changed twice per week.

As the mononuclear cell was cultured in the differentiation medium, the morphological change of the mononuclear cell was not detected after about 1 week. The neural cell colony was appeared after about 4 weeks, and proliferated continuously. A neuron with long axon and short dendrite, and an astrocyte with only short dendrite were observed after about 8 weeks. Further, from about 8 weeks, Example 3 was confirmed to proliferate maintaining same morphology even in a medium comprising only epithermal growth factor.

In contrast to culturing in the medium comprising the epithermal growth factor and the hepatocyte growth factor, the mononuclear cell was not differentiated into the neural cell in the medium comprising only the epithermal growth factor, and was differentiated early and thus the mononuclear cell was not proliferated in the medium comprising only the hepatocyte growth factor.

Table 1 in below showed number of cell proliferated after the mononuclear cell was cultured in the medium comprising the epithermal growth factor and the hepatocyte growth factor for about 4 weeks without confluent culture, and Table 2 showed the proliferating conduct of the cell after cell pretreated in Table 1 was cultured in a medium comprising only the epithermal growth factor or the hepatocyte growth factor for about 4 and about 8 weeks, respectively (a number of cell inoculated the early is about 1×10$^5$).

EXAMPLE 4

Differentiation of the Mononuclear Cell into the Neural Cell After Confluent Culture Example 4 was confirmed that the mononuclear cell cultured in Example 2 was differentiated into the neural cell in a differentiation medium comprising about 10 ng/ml of the epithermal growth factor (Gibco BRL) and about 20 ng/ml of the hepatocyte growth factor (R&D systems) after confluent culture for about 24 hours. Then the differentiation medium was changed twice per week.

As the mononuclear cell was cultured in the differentiation medium, the neural cell colony started to be appeared after about 1 week, and proliferated continuously (refer to FIG. 1). As the mononuclear cell was cultured in the differentiation medium, a neuron with long axon and short dendrite, and an astrocyte with only short dendrite were observed after about 2 weeks (refer to FIGS. 2 and 3). Further, from about 2 weeks, Example 4 was confirmed to proliferate maintaining same morphology even in a medium comprising only the epithermal growth factor.

In contrast to culture in the medium comprising the epithermal growth factor and the hepatocyte growth factor, the mononuclear cell was not differentiated into the neural cell in the medium comprising only the epithermal growth factor, and was differentiated early and so not proliferated in the medium comprising only the hepatocyte growth factor.

Table 1 showed number of cell proliferated after the mononuclear cell was cultured in the medium comprising the epithermal growth factor and the hepatocyte growth factor for about 2 weeks after confluent culture for about 24 hours, and Table 2 showed number of cell conducted proliferating after cells were cultured in the medium comprising only the epithermal growth factor or the hepatocyte growth factor for about 4 and about 8 weeks, respectively, as pretreated (number of cell inoculated the early is about $1 \times 10^5$).

MAP-2 (microtubule-associated protein-2) antibody were used. After reacting to first antibody, the first antibody unbounded antibody was removed and the cells reacted to the first antibody were washed with 0.1M PBS comprising 0.5% by weight BSA for about 5 minutes twice. Second antibody was added to the cells reacted to the first antibody and the cells added with the second antibody were incubated for about 30 minutes. The incubated cells were then washed with 0.1M PBS comprising 0.5% by weight BSA for about 15 minutes twice. Vectastain Elite ABC kit (Vector Laboratory Inc.) comprising Avidin-biotin was used and reacted to the incubated cells for about 30 minutes. The reacted cells were washing with 0.1M PBS for about 5 minutes twice, and reacted to DAB (3,3'-diaminobenzidine tetrahydrochloride dehydrate, Sigma) as color-developing substrate for about 5 minutes. 0.1M PBS was added to the cells reacted to DAB for about 5 minutes in order to stop the reaction, and the cells quenching the reaction were washed with the 0.1M PBS for about 5 minutes twice. The reactant was dried and washed with distilled $H_2O$. The dried reactant was then dehydrated with distilled $H_2O$, 70%, 80%, 95% and 100% by weight ethanol in that order and fixed.

As a result of immunocytochemistry, FIG. 4 showed that the differentiated cell was stained positively in a neuron marker such as NeuN, NSE, MAP-2, and tubulin III and in an

TABLE 1

| Pretreatment | Time (week) | Number of cell inoculated | Only HGF | Only EGF | EGF and HGF |
|---|---|---|---|---|---|
| Non-confluent culture | 4 | $7.5 \times 10^7$ | Not proliferated | $1 \times 10^5$ | $2.0 \times 10^5$ |
| Confluent culture | 2 | $7.5 \times 10^7$ | Not proliferated | $1.2 \times 10^5$ | $1.8 \times 10^5$ |

TABLE 2

| Pretreatment | Time (week) | Only HGF | Only EGF | EGF and HGF |
|---|---|---|---|---|
| Non-confluent culture | 4 | Not proliferated | $2 \times 10^5$ | $2 \times 10^5$ |
|  | 8 | Not proliferated | $5 \times 10^5$ | $1 \times 10^5$ |
| Confluent culture | 4 | Not proliferated | $2 \times 10^5$ | $1.7 \times 10^5$ |
|  | 8 | Not proliferated | $5 \times 10^5$ | $1.3 \times 10^5$ |

EXAMPLE 5

Immunocytochemistry I

The cells differentiated in Examples 3 and 4 were adhered on the surface of a cover glass at about $1 \times 10^4$ cells/cm². Subsequently, the cells were washed with 0.1M phosphate buffer for about 5 minutes, fixed with 0.1M phosphate buffer comprising 4% by weight paraformaldehyde for about 15 minutes, and washed with 0.1M PBS (phosphate buffered saline) for about 15 minutes twice. Then, the fixed cells were treated with 0.1M PBS comprising 0.1% by weight bovine serum albumin (BSA) and 0.2% by weight triton X-100 for about 5 minutes, first antibody was added to the fixed cells, and the fixed cells and the first antibody were reacted for about 16 hours. As for the first antibody, anti-human neuron-specific enolase (NSE; Chemicon), anti-human NeuN (Chemicon), anti-human tubulin III (Sigma), anti-human glial fibrillary acidic protein (GFAP; Sigma), and anti-human astrocyte marker such as GFAP, whereas the differentiated cell was stained negatively in a microglia marker such as OX-42. The result showed that the mononuclear cell was differentiated into the neuron and the astrocyte not only morphologically but also biochemically in the medium comprising the epithermal growth factor and the hepatocyte growth factor, however, the mononuclear cell was not differentiated into a microglial cell.

The mononuclear cell was cultured in a medium comprising only the epithermal growth factor, a medium comprising the epithermal growth factor and the hepatocyte growth factor, and a medium comprising the epithermal growth factor and the hepatocyte growth factor after confluent cultured for about 24 hours, respectively. Subsequently, the differentiated cell was stained by immunocytochemistry to observe a ratio of the neuron (stained positively in NeuN, NSE, MAP-2 and tubulin III) and the astrocyte (stained positively in GFAP). The result was shown in Table 3.

TABLE 3

|  | Time (week) | NSE | NeuN | GFAP | Map 2 | Negative cells |
|---|---|---|---|---|---|---|
| Only EGF | 4 | 0.9% | 0.8% | 1.2% | — | 89% |
| EGF + HGF | 2 | 10% | 25% | 4% | — | 70% |
| EGF + HGF | 4 | 56% | 75% | 24% | — | 20% |
| EGF + HGF After confluent culture for 24 hours, | 2 | 62% | 88% | 31% | 11% | 10% |

As shown in Table 3, when the mononuclear cell was differentiated in the medium comprising the epithermal growth factor and the hepatocyte growth factor for about 2 weeks after confluent culture for about 24 hours, about 80% by count of cells were differentiated into the neural cell; about 70% by count of the neural cell is the neuron and about 30% by count is the astrocyte.

EXAMPLE 6

Isolation and Culture of the Mesenchymal Stem Cell

To confirm whether the mesenchymal cell was differentiated into the neural cell, the mesenchymal cell was isolated from the bone marrow-derived mononuclear cell and an experimentation of differentiative potential was carried out.

The mononuclear cell cultured in Example 2 was inoculated in a culture flask of about $1\times10^6$ cells/cm$^2$ and incubated at a temperature of about 37° C. in $CO_2$ incubator. As a medium, Gibco BRL (DMEM) of low glucose concentration with fetal bovine serum (FBS) of about 10% by weight was added to the medium. After culturing of the mononuclear cell for about 1 to about 2 weeks, the mononuclear cell was fully proliferated for a subculture, and the mononuclear cell continued to proliferate after 20 subculturings.

The mononuclear cell group derived from the bone marrow contains leukocyte, lymphocyte, osteoblast, chondroblast, muscle cell, fibroblast, fat cell and stem cell. The stem cell may be differentiated into the leukocyte, lymphocyte, osteoblast, chondroblast, muscle cell, fibroblast, fat cell, etc. The stem cell indicates hematopoietic stem cell and mesenchymal stem cell. The hematopoietic stem cells of forming blood cell such as erythrocyte, leucocyte and lymphocyte are not continually proliferated in a normal culture medium, and are differentiated into a mature cell such that continually proliferating cell is the mesenchymal stem cell.

To confirm, Example 6 examined whether the above-obtained cells have differentiative potential of the mesenchymal stem cell by adding kinds of cytokines. That is, possibility of differentiation into connective tissue such as osteoblasts, chondroblasts and fat cell was tested.

To differentiate into osteoblast, the above-obtained cells adding kinds of cytokines were incubated with 100 mM dexamethasone, 10 mM glycerol phosphate, 50 nM ascorbate-2-phosphate, and 10% by weight fetal bovine serum (FBS). To differentiate into chondroblast, the incubated cells were centrifuged at 1500 rpm for about 10 minutes such that the incubated cells were formatted as pellet and then the pellet was added with 100 nM dexamethasone and 10 ng/ml TGF-3 in serum-free state. To differentiate into fat cell, the above-obtained cells adding kinds of cytokines were incubated with 0.5 mM 1-methyl-3-isobutylxanthine, 1 mM dexamethasone, 10 g/ml insuli, and 10 nM indomethacine (Pittenger et al., Science 284:143-147, 1999). Differentiation into each cell was confirmed by alkaline phosphatase staining in osteoblast (Jaiswal et al., J. Cell Biochem. 64(2) 143-147, 1999), type II collagen staining RT-PCR by Toluidine blue in chondroblast (Mackay et al., Tissue Eng. 4(4): 415-428, 1998), and oil red O staining in fat cell, respectively.

As a result shown in FIGS. 5a, 5b, and 5c, all were positively stained. The mesenchymal stem cell cultured ex vivo still had differentiative potential into connective tissue such as osteoblasts, chondroblasts and fat cell.

EXAMPLE 7

Differentiation of the Mesenchymal Stem Cell into the Neural Cell Without Confluent Culture To confirm whether the mesenchymal stem cell isolated in Example 6 differentiated into the neural cell, the mesenchymal stem cell cultured ex vivo in DMEM of low glucose concentration, the DMEM comprising 10% by weight FBS, was cultured in the differentiation medium comprising about 10 ng/ml of the epithermal growth factor and about 20 ng/ml of the hepatocyte growth factor as the method of Example 3 for 8 weeks without confluent culturing.

The result was same as the neural cell differentiated from the bone marrow-derived mononuclear stem cell; morphological change was not detected after about 1 week, and the neural cell colony was appeared after about 4 weeks, and continually proliferated after about 5 weeks. After about 8 weeks, Example 7 confirmed to proliferate as in same morphology even in case of culturing in the medium comprising only the epithermal growth factor.

EXAMPLE 8

Differentiation of the Mesenchymal Stem Cell into the Neural Cell after Confluent Culture To confirm whether the mesenchymal stem cell isolated in Example 6 differentiated into neural cell, the mesenchymal stem cell, cultured ex vivo in DMEM of low glucose concentration, the DMEM comprising 10% by weight FBS, was cultured in the differentiation medium comprising about 10 ng/ml of the epithermal growth factor and about 20 ng/ml of the hepatocyte growth factor as the method of Example 4 for about 2 weeks after confluent culture for about 24 hours.

The result was same as the neural cell differentiated from the bone marrow-derived mononuclear stem cell; morphological change was not detected after about 1 week, and continually proliferated after about 2 weeks (refer to FIGS. 6 and 7). After about 2 weeks, Example 8 confirmed to proliferate as same morphology even in case of culturing in the medium comprising only the epithermal growth factor.

EXAMPLE 9

Immunocytochemistry II

The cell differentiated in Examples 7 and 8 was stained by immunocytochemistry as the method of Example 5. The result was same as the neural cell differentiated from the bone marrow-derived mononuclear stem cell; the neural cell differentiated from the mesenchymal stem cell was stained positively in the neuron marker such as NeuN, NSE, MAP-2, and tubulin III and in the astrocyte marker such as GFAP (FIGS. 8a, 8b, 8c, and 8d). In case of performing a confluent culture as pre-treatment, the result showed that mesenchymal stem cell was differentiated into the neuron and the astrocyte, and that differentiation rate was faster by 2 times and efficiency of differentiation was increased by 80% to 90% than in case of without performing the confluent culture as pre-treatment.

EXAMPLE 10

To confirm whether function of the neural cell differentiated from the mesenchymal stem cell was equal to function of human neural cell, Example 10 was carried out by reaching and fixing damaged portion when the neural cell was implanted into damaged portion of animal.

To induce Ischemic brain disease, known as common neurodegenerative disease in human, a brain of an experimental rat was cut middle cerebral artery was fastened for 1 hour and loosened again such that the brain of the experimental rat was taken local Ischmic disease in cerebrum cortex. And then the neural cell prepared by the method of Example 8 was venous-injected at about $3\times10^5$ cells. Then the injected neural cell was stained to distinguish from other cells with LacZ.

After 1 week since the venous injection, the brain of the experimental rat was cut and observed through optical microscope. The result was shown in FIG. 9; FIG. 9a showed a photograph of rat brain before inducing local Ischemic disease, FIG. 9b showed a photograph of rat brain in 2 weeks after since the neural cells were venous-injected after inducing local Ischemic disease, and FIG. 9c showed an enlarged photograph of local Ischemic portion in FIG. 9b.

As shown in FIGS. 9a and 9b, difference between normal and Ischemic brain was clearly confirmed. Especially, it was detected that cells stained in weakly in FIGS. 9b and 9c was stained strongly with LacZ. Accordingly, the neural cell was selectively arrived at damaged portion. That is, the mesenchymal stem cell was normally differentiated into the neural cell and the neural cell was located in appropriate portion. Therefore, the neural cell differentiated in the present invention is useful for neurodegenerative disease.

INDUSTRIAL APPLICABILITY

As mentioned above, the present invention provides more effective method of differentiating and proliferating a mesenchymal stem cell or a mononuclear cell into a neural cell consisting of a neuron and an astrocyte in terms of time, efficiency and maturity, and sufficient amount of neural cells to produce a pharmaceutical composition for treating neurodegenerative disease. A method is safe and has little problem with clinical application due to using a natural compound in a cell. The method has effects on little immunological response and suppling a sufficient amount of neural cells due to obtaining a large quantity of neural cells from patient's bone marrow.

The invention claimed is:

1. A method of differentiating and proliferating a mesenchymal stem cell into a neural cell, said method comprising two steps of:
   (1) confluent culturing the mesenchymal stem cell as a pretreatment and
   (2) culturing a mesenchymal stem cell in a medium comprising growth factors,
   wherein the growth factor are epithermal growth factor and hepatocyte growth factor;
   whereby the confluent mesenchymal stem cell differentiates into a neural cell.

2. The method of claim 1, wherein the mesenchymal stem cell is cultured for more than 1 week in a medium comprising about 1 to about 10,000 ng/ml by concentration of the epithermal growth factor and about 1 to about 10,000 ng/ml by concentration of the hepatocyte growth factor after confluent culturing the mesenchymal stem cell for about 1 to about 50 hours.

3. The method of claim 1, wherein the mesenchymal stem cell is cultured for more than 1 week in a medium comprising about 10 ng/ml by concentration of the epithermal growth factor and about 20 ng/ml by concentration of the hepatocyte growth factor after confluent culturing the mesenchymal stem cell for about 24 hours.

4. The method of claim 1, wherein the mesenchymal stem cell is cultured for about 2 weeks in the medium comprising growth factor, wherein the growth factor are epithermal growth factor and hepatocyte growth factor, and then the medium comprising the epithermal growth factor and the hepatocyte growth factor is changed with a medium consisting of the epithermal growth factor.

5. The method of claim 4, wherein the mesenchymal stem cell is a mononuclear cell comprising the mesenchymal stem cell obtained from the bone marrow.

* * * * *